United States Patent [19]
Kohnert et al.

[11] Patent Number: 5,973,118
[45] Date of Patent: Oct. 26, 1999

[54] **MUTANT OF THE *ERYTHRINA CAFFRA* TYPE INHIBITOR AND THE USE OF THE SAID MUTANT FOR PURIFYING SERINE PROTEASES**

[75] Inventors: Ulrich Kohnert, Habach; Anne Stern, Penzberg; Manfred Wozny, Weilheim; Stephan Fischer, Polling, all of Germany

[73] Assignee: Roche Diagnostics GmbH, Mannheim, Germany

[21] Appl. No.: 08/943,814

[22] Filed: Oct. 3, 1997

Related U.S. Application Data

[63] Continuation-in-part of application No. PCT/EP96/01388, Mar. 29, 1996.

[30] Foreign Application Priority Data

Apr. 6, 1995 [DE] Germany .............. 195 12 937

[51] Int. Cl.$^6$ .............. C07K 1/00; A61K 38/00; A61K 35/78
[52] U.S. Cl. .............. 530/350; 530/344; 530/370; 530/379
[58] Field of Search .............. 435/69.2, 219, 435/226; 514/2, 12; 530/350, 344, 370, 379

[56] References Cited

FOREIGN PATENT DOCUMENTS 0 218 479  10/1986  European Pat. Off. .

OTHER PUBLICATIONS

Teixeria et al., Biochimica et Biophysia Acta, vol. 1217, (1994) pp. 23–28, "Site–directed mutagenesis of the synthetic Erythrina trypsin/tissue plasminogen activator (tPA) inhibitor . . . ".

*Primary Examiner*—Bradley L. Sisson
*Assistant Examiner*—Einar Stole
*Attorney, Agent, or Firm*—Nikaido Marmelstein Murray & Oram, LLP

[57] ABSTRACT

A polypeptide which has the activity of an inhibitor DE-3 from *Erythrina caffra* and which reversibly and selectively binds serine proteases from a protein mixture is obtainable by culturing prokaryotic or eukaryotic host cells which have been transformed or transfected with a nucleic acid that codes for the said polypeptide in a manner that allows the host cells to express the said polypeptide under suitable nutrient conditions and isolating the said polypeptide, wherein the polypeptide has an amino acid sequence which is functionally analogous to SEQ ID NO:2, has a partial region that is more than 85% homologous to the region of amino acids 39–139 of this sequence, has two disulfide bridges and begins N-terminally with SEQ ID NO:4 or with a SEQ ID NO:4 extended N-terminally by methionine and has a binding capacity for tissue plasminogen activators of 1.25 MU/ml and more and is particularly suitable for purifying plasminogen activators such as tissue plasminogen activators (t-PA and derivatives).

6 Claims, No Drawings

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 516 base pairs (B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION:1..516

(xi) SEQUENCE DESCRIPTION: SEQ ID NO: 1:

| | | | | | | | | | | | | | | | | |
|---|---|---|---|---|---|---|---|---|---|---|---|---|---|---|---|---|
| TCA | TTA | TTA | GAT | GGT | AAC | GGC | GAA | GTG | GTG | CAG | AAC | GGC | GGT | ACC | TAT | 48 |
| Ser | Leu | Leu | Asp | Gly | Asn | Gly | Glu | Val | Val | Gln | Asn | Gly | Gly | Thr | Tyr | |
| 1 | | | | 5 | | | | | 10 | | | | | 15 | | |
| TAT | CTG | CTG | CCG | CAG | GTG | TGG | GCG | CAG | GGC | GGC | GGC | GTG | CAG | CTG | GCG | 96 |
| Tyr | Leu | Leu | Pro | Gln | Val | Trp | Ala | Gln | Gly | Gly | Gly | Val | Gln | Leu | Ala | |
| | | | 20 | | | | | 25 | | | | | 30 | | | |
| AAA | ACC | GGC | GAA | GAA | ACC | TGC | CCG | CTG | ACC | GTG | GTG | CAG | AGC | CCG | AAC | 144 |
| Lys | Thr | Gly | Glu | Glu | Thr | Cys | Pro | Leu | Thr | Val | Val | Gln | Ser | Pro | Asn | |
| | | 35 | | | | | 40 | | | | | 45 | | | | |
| GAA | CTG | AGC | GAT | GGC | AAA | CCG | ATT | CGT | ATT | GAA | AGC | CGT | CTG | CGT | AGC | 192 |
| Glu | Leu | Ser | Asp | Gly | Lys | Pro | Ile | Arg | Ile | Glu | Ser | Arg | Leu | Arg | Ser | |
| | 50 | | | | | 55 | | | | | 60 | | | | | |
| GCG | TTT | ATT | CCG | GAT | GAT | GAT | AAA | GTG | CGT | ATT | GGC | TTT | GCG | TAT | GCG | 240 |
| Ala | Phe | Ile | Pro | Asp | Asp | Asp | Lys | Val | Arg | Ile | Gly | Phe | Ala | Tyr | Ala | |
| 65 | | | | 70 | | | | | 75 | | | | | 80 | | |
| CCG | AAA | TGC | GCG | CCG | AGC | CCG | TGG | TGG | ACC | GTG | GTG | GAA | GAT | GAA | CAG | 288 |
| Pro | Lys | Cys | Ala | Pro | Ser | Pro | Trp | Trp | Thr | Val | Val | Glu | Asp | Glu | Gln | |
| | | | 85 | | | | | 90 | | | | | 95 | | | |
| GAA | GGC | CTG | AGC | GTG | AAA | CTG | AGC | GAA | GAT | GAA | AGC | ACC | CAG | TTT | GAT | 336 |
| Glu | Gly | Leu | Ser | Val | Lys | Leu | Ser | Glu | Asp | Glu | Ser | Thr | Gln | Phe | Asp | |
| | | | 100 | | | | | 105 | | | | | 110 | | | |
| TAT | CCG | TTT | AAA | TTT | GAA | CAG | GTG | AGC | GAT | CAG | CTG | CAT | AGC | TAT | AAA | 384 |
| Tyr | Pro | Phe | Lys | Phe | Glu | Gln | Val | Ser | Asp | Gln | Leu | His | Ser | Tyr | Lys | |
| | | 115 | | | | | 120 | | | | | 125 | | | | |
| CTG | CTG | TAT | TGC | GAA | GGC | AAA | CAT | GAA | AAA | TGC | GCG | AGC | ATT | GGC | ATT | 432 |
| Leu | Leu | Tyr | Cys | Glu | Gly | Lys | His | Glu | Lys | Cys | Ala | Ser | Ile | Gly | Ile | |
| | 130 | | | | | 135 | | | | | 140 | | | | | |
| AAC | CGT | GAT | CAG | AAA | GGC | TAT | CGT | CGT | CTG | GTG | GTG | ACC | GAA | GAT | TAT | 480 |
| Asn | Arg | Asp | Gln | Lys | Gly | Tyr | Arg | Arg | Leu | Val | Val | Thr | Glu | Asp | Tyr | |
| 145 | | | | 150 | | | | | 155 | | | | | 160 | | |
| CCG | CTG | ACC | GTG | GTG | CTG | AAA | AAA | GAT | GAA | AGC | AGC | | | | | 516 |
| Pro | Leu | Thr | Val | Val | Leu | Lys | Lys | Asp | Glu | Ser | Ser | | | | | |
| | | | 165 | | | | | 170 | | | | | | | | |

(2) INFORMATION FOR SEQ ID NO: 2:

(i) SEQUENCE CHARACTERISTICS:
(A) LENGTH: 172 amino acids
(B) TYPE: amino acid
(D) TOPOLOGY: linear (ii) MOLECULE TYPE: protein (xi) SEQUENCE DESCRIPTION: SEQ ID NO: 2:

| | | | | | | | | | | | | | | |
|---|---|---|---|---|---|---|---|---|---|---|---|---|---|---|
| Ser | Leu | Leu | Asp | Gly | Asn | Gly | Glu | Val | Val | Gln | Asn | Gly | Gly | Thr | Tyr |
| 1 | | | | 5 | | | | | 10 | | | | | 15 | |
| Tyr | Leu | Leu | Pro | Gln | Val | Trp | Ala | Gln | Gly | Gly | Gly | Val | Gln | Leu | Ala |
| | | | 20 | | | | | 25 | | | | | 30 | | |
| Lys | Thr | Gly | Glu | Glu | Thr | Cys | Pro | Leu | Thr | Val | Val | Gln | Ser | Pro | Asn |
| | | 35 | | | | | 40 | | | | | 45 | | | |
| Glu | Leu | Ser | Asp | Gly | Lys | Pro | Ile | Arg | Ile | Glu | Ser | Arg | Leu | Arg | Ser |
| | 50 | | | | | 55 | | | | | 60 | | | | |

```
Ala Phe Ile Pro Asp Asp Lys Val Arg Ile Gly Phe Ala Tyr Ala
 65                  70                  75                  80

Pro Lys Cys Ala Pro Ser Pro Trp Trp Thr Val Val Glu Asp Glu Gln
                 85                  90                  95

Glu Gly Leu Ser Val Lys Leu Ser Glu Asp Glu Ser Thr Gln Phe Asp
                100                 105                 110

Tyr Pro Phe Lys Phe Glu Gln Val Ser Asp Gln Leu His Ser Tyr Lys
            115                 120                 125

Leu Leu Tyr Cys Glu Gly Lys His Glu Lys Cys Ala Ser Ile Gly Ile
        130                 135                 140

Asn Arg Asp Gln Lys Gly Tyr Arg Arg Leu Val Val Thr Glu Asp Tyr
145                 150                 155                 160

Pro Leu Thr Val Val Leu Lys Lys Asp Glu Ser Ser
                165                 170
```

(2) INFORMATION FOR SEQ ID NO: 3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Val Leu Leu Asp
 1
```

(2) INFORMATION FOR SEQ ID NO: 4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Ser Leu Leu Asp
 1
```

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(xi) SEQUENCE DESCRIPTION: SEQ ID NO: 5:

AAAGGATCCC TCGAGAAATC ATAAAAA                                   27

(2) INFORMATION FOR SEQ ID NO: 6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(xi) SEQUENCE DESCRIPTION: SEQ ID NO: 6:

CATAAGAATT CTGTTTCCTC TTTAATGAAT TCTG                                        34

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "primer"

(xi) SEQUENCE DESCRIPTION: SEQ ID NO: 7:

CAGAATTCTT ATGTCATTAT TAGA                                                   24

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(xi) SEQUENCE DESCRIPTION: SEQ ID NO: 8:

AGAAGCTTTT ATCAGCTG                                                          18

(2) INFORMATION FOR SEQ ID NO: 9:

(i) SEQUENCE CHARACTERISTICS:
        (A) LENGTH: 541 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION:11..529

(ix) FEATURE:
        (A) NAME/KEY: mat_peptide
        (B) LOCATION:11

(xi) SEQUENCE DESCRIPTION: SEQ ID NO: 9:

```
CAGAATTCTT ATG TCA TTA TTA GAT GGT AAC GGC GAA GTG GTG CAG AAC              49
           Met Ser Leu Leu Asp Gly Asn Gly Glu Val Val Gln Asn
            1               5                  10

GGC GGT ACC TAT TAT CTG CTG CCG CAG GTG TGG GCG CAG GGC GGC GGC             97
Gly Gly Thr Tyr Tyr Leu Leu Pro Gln Val Trp Ala Gln Gly Gly Gly
 15                  20                  25

GTG CAG CTG GCG AAA ACC GGC GAA GAA ACC TGC CCG CTG ACC GTG GTG            145
Val Gln Leu Ala Lys Thr Gly Glu Glu Thr Cys Pro Leu Thr Val Val
 30                  35                  40                  45

CAG AGC CCG AAC GAA CTG AGC GAT GGC AAA CCG ATT CGT ATT GAA AGC            193
Gln Ser Pro Asn Glu Leu Ser Asp Gly Lys Pro Ile Arg Ile Glu Ser
             50                  55                  60

CGT CTG CGT AGC GCG TTT ATT CCG GAT GAT GAT AAA GTG CGT ATT GGC            241
Arg Leu Arg Ser Ala Phe Ile Pro Asp Asp Asp Lys Val Arg Ile Gly
             65                  70                  75

TTT GCG TAT GCG CCG AAA TGC GCG CCG AGC CCG TGG TGG ACC GTG GTG            289
Phe Ala Tyr Ala Pro Lys Cys Ala Pro Ser Pro Trp Trp Thr Val Val
```

```
                      80                  85                    90
GAA GAT GAA CAG GAA GGC CTG AGC GTG AAA CTG AGC GAA GAT GAA AGC        337
Glu Asp Glu Gln Glu Gly Leu Ser Val Lys Leu Ser Glu Asp Glu Ser
         95                 100                 105

ACC CAG TTT GAT TAT CCG TTT AAA TTT GAA CAG GTG AGC GAT CAG CTG        385
Thr Gln Phe Asp Tyr Pro Phe Lys Phe Glu Gln Val Ser Asp Gln Leu
110             115                 120                 125

CAT AGC TAT AAA CTG CTG TAT TGC GAA GGC AAA CAT GAA AAA TGC GCG        433
His Ser Tyr Lys Leu Leu Tyr Cys Glu Gly Lys His Glu Lys Cys Ala
                130                 135                 140

AGC ATT GGC ATT AAC CGT GAT CAG AAA GGC TAT CGT CGT CTG GTG GTG        481
Ser Ile Gly Ile Asn Arg Asp Gln Lys Gly Tyr Arg Arg Leu Val Val
            145                 150                 155

ACC GAA GAT TAT CCG CTG ACC GTG GTG CTG AAA AAA GAT GAA AGC AGC        529
Thr Glu Asp Tyr Pro Leu Thr Val Val Leu Lys Lys Asp Glu Ser Ser
        160                 165                 170

TGATAAAAGC TT                                                           541
```

(2) INFORMATION FOR SEQ ID NO: 10:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ser Leu Leu Asp Gly Asn Gly Glu Val Val Gln Asn Gly Gly Thr
 1               5                  10                  15

Tyr Tyr Leu Leu Pro Gln Val Trp Ala Gln Gly Gly Val Gln Leu
            20                  25                  30

Ala Lys Thr Gly Glu Glu Thr Cys Pro Leu Thr Val Val Gln Ser Pro
        35                  40                  45

Asn Glu Leu Ser Asp Gly Lys Pro Ile Arg Ile Glu Ser Arg Leu Arg
    50                  55                  60

Ser Ala Phe Ile Pro Asp Asp Lys Val Arg Ile Gly Phe Ala Tyr
65                  70                  75                  80

Ala Pro Lys Cys Ala Pro Ser Pro Trp Trp Thr Val Val Glu Asp Glu
                85                  90                  95

Gln Glu Gly Leu Ser Val Lys Leu Ser Glu Asp Glu Ser Thr Gln Phe
               100                 105                 110

Asp Tyr Pro Phe Lys Phe Glu Gln Val Ser Asp Gln Leu His Ser Tyr
           115                 120                 125

Lys Leu Leu Tyr Cys Glu Gly Lys His Glu Lys Cys Ala Ser Ile Gly
       130                 135                 140

Ile Asn Arg Asp Gln Lys Gly Tyr Arg Arg Leu Val Val Thr Glu Asp
145                 150                 155                 160

Tyr Pro Leu Thr Val Val Leu Lys Lys Asp Glu Ser Ser
               165                 170
```

MUTANT OF THE *ERYTHRINA CAFFRA* TYPE INHIBITOR AND THE USE OF THE SAID MUTANT FOR PURIFYING SERINE PROTEASES

CROSS REFERENCE TO RELATED APPLICATION

This application is a continuation-in-part of International Application PCT/EP96/01388, filed Mar. 29, 1996, and designating the U.S. and claims benefits of German Application No. 19512937.7 filed Apr. 6, 1995.

The invention concerns a new inhibitor of the Erythrina caffra type and its use to purify serine proteases.

Immobilized trypsin inhibitors from erythrina (ETI) are effective reagents for the purification by affinity chromatography of serine proteases and especially of plasminogen activators (C. Heussen (1984) (22)), β-trypsin, α-chymotrypsin and thrombin (S. Onesti et al. (1992) (34)). These trypsin inhibitors have been known for a long time (C. Heussen (1982) (23); F. J. Joubert (1982) (26); F. J. Joubert (1982) (27)).

The inhibitor DE-3 from *E. caffra* is particularly preferably suitable for the purification of plasminogen activators (F. J. Joubert (1987) (25)). The complete amino sequence of this inhibitor is also described in this publication. DE-3 can be isolated and purified from the seeds of *E. caffra* (F. J. Joubert (1982) (26)). An ETI which is not cytotoxic is described in EP-B 0 218 479 (15).

A recombinant ETI is described by Teixeira et al. (1994) (45) the specific inhibitory activity of which for tissue plasminogen activator is $1.7 \times 10^9$ U/mmol. In contrast the specific inhibitory activity of natural ETI is $1.94 \times 10^9$ U/mmol. The same applies to the inhibitory activity towards trypsin ($2.63 \times 10^{12}/3.21 \times 10^{12}$). Thus the specific inhibitory activity of recombinant ETI produced according to Teixeira is 20% less for trypsin and 10% less for tissue plasminogen activator than the activity of natural ETI.

A modified form of ETI is described by Teixeira et al (1994) (46) in which the N-terminal Val is replaced by Asp. Such a modified ETI does not bind to tPA and shows no inhibitory activity towards tPA. The specific inhibitory activity towards trypsin is practically identical for natural ETI and Asp-modified ETI.

According to Teixeira recombinant ETI is obtained by expression and purified by an ammonium sulfate precipitation (80% saturation), dialysis against water and a cyanogen bromide cleavage in which the N-terminal sequence including the methionine is cleaved off. It is subsequently purified by gel filtration (Sephadex G50).

A purified polypeptide which has the activity of an inhibitor DE-3 from *Erythrina caffra* (also denoted ETI polypeptide in the following) is described in DE-A44 24 171.2 (9) which, in contrast to the inhibitor isolated from natural sources, has a considerably higher specificity towards serine proteases.

A further important criterium for the suitability of an ETI polypeptide for the effective purification of serine proteases is the binding capacity for serine proteases.

The object of the invention is therefore to improve the effectivity of the binding capacity of an ETI polypeptide for the purification of serine proteases. The invention concerns a polypeptide which has the activity of an inhibitor DE-3 from *Erythrina caffra*, reversibly and selectively binds a serine protease from a protein mixture wherein the polypeptide has an amino acid sequence which is functionally analogous to SEQ ID NO:2, has a partial region that is more than 85% homologous to the region of amino acids 39–139 of this sequence, has two disulfide bridges and begins N-terminally with Ser and preferably with SEQ ID NO:4. The binding capacity of this polypeptide for plasminogen activators is 1.25 MU/ml and more.

A polypeptide according to the invention is preferably coded
a) by a nucleic acid according to SEQ ID NO:1,
b) by a nucleic acid that hybridizes under stringent conditions with a DNA sequence complementary to the DNA sequence shown in SEQ ID NO:1 and begins N-terminally with a nucleic acid sequence which codes for SEQ ID NO:4,
c) by a nucleic acid which would hybridize under stringent conditions with one of the sequence mentioned in a) or b) without the degeneracy of the genetic code.

It has surprisingly turned out that the binding capacity for serine proteases is considerably increased by substituting the N-terminal Val by Ser in an ETI polypeptide. Whereas the known ETI polypeptide begins N-terminally with the amino acid sequence Val-Leu-Leu-ASP (SEQ-ID-NO:3), the ETI polypeptide according to the invention begins with Ser-Leu-Leu-Asp (SEQ-ID-NO:4).

These results are particularly surprising with regard to Teixeira et al. (1994) (46). A person skilled in the art would have to expect from these publications that the modification of the N-terminus of ETI would result in a modified ETI that has lost its specific inhibitory activity towards plasminogen activators and that its activity towards trypsin remains unchanged. It is thus even more surprising that the specific activity for trypsin as well as the binding capacity for plasminogen activators and in particular for tissue plasminogen activators increases to a significant extent for a modified ETI according to the invention.

"A polypeptide with the activity of an inhibitor DE-3 from *Erythrina caffra*" is understood as a polypeptide which specifically binds serine proteases such as plasminogen activators, β-trypsin, α-chymotrypsin and/or thrombin. The binding can inhibit the activity of the serine protease.

A "functionally analogous" ETI polypeptide is understood as a polypeptide which has the activity of an inhibitor DE-3 from *Erythrina caffra*. Modifications of the protein sequence are possible within the usual framework familiar to a person skilled in the art. However, in this connection it should be noted that the N-terminus should be identical to SEQ ID NO:4 (N-terminal Ser) and that the polypeptide must have two disulfide bridges to fix the spatial structure. After recombinant production in prokaryotes the protein according to the invention can also further contain an N-terminal methionine (SEQ ID NO:10). The positions of these disulfide bridges should correspond to those of the disulfide bridges of the ETI polypeptide (Cys 39–Cys 83 and Cys 132–Cys 139, Lehle, K. et al. (1994) (30)). Equally a partial region of the ETI polypeptide should be more than 85% homologous to the sequence region 39–139 of SEQ ID NO:2. This partial region is preferably also the sequence region 39–139 of the protein according to the invention and is preferably identical or essentially identical to the sequence region 39–139 from SEQ ID NO:2.

An ETI polypeptide (or a nucleic acid that codes for such a polypeptide) is particularly preferably used whose amino acid sequence is identical or essentially identical to SEQ ID NO:2. It has surprisingly also turned out that the binding capacity of the inhibitor for serine proteases is particularly high when, after recombinant production in prokaryotes, the N-terminal methionine is completely cleaved off or at least to a large extent (preferably by more than 85% in the ETI polypeptide preparation). The ETI polypeptide can differ in size. However, it preferably comprises 100–200 amino acids, particularly preferably about 139–173 amino acids.

The binding capacity of an inhibitor for serine proteases is understood as the amount of a serine protease (preferably a plasminogen activator) which can be removed from a solution by an immobilized inhibitor. The binding capacity is usually expressed as activity/ml matrix [in the case of plasminogen activators as amidolytic activity stated in U/ml matrix]. The activity of the plasminogen activator is determined after elution of the previously bound serine protease.

The activity is determined according to U. Kohnert et al. (1992) (29). For this the rate of cleavage of H-D-Ile-Pro-Arg-p-nitroanilide dihydro-chloride (S2288, Kabi Vitrum, Sweden) is measured photometrically via the absorbance at 405 nm.

The invention also concerns a process for the purification of a serine protease from a protein mixture by binding the serine protease to an immobilized ETI polypeptide which reversibly and selectively binds serine proteases, removing the unbound fractions from the protein mixture, detaching the serine protease from the inhibitor, separating the immobilized inhibitor from the soluble serine protease and isolating the serine protease which is characterized in that an ETI polypeptide is used which reversibly and selectively binds serine proteases from a protein mixture and wherein the polypeptide preferably has an amino acid sequence which is functionally analogous to SEQ ID NO:2, has a partial region that is more than 85% homologous to the region of amino acids 39–139 of this sequence, has two disulfide bridges and begins N-terminally with SEQ ID NO:4 or with a SEQ ID NO:4 extended N-terminally by methionine.

Such an ETI polypeptide is preferably produced by prokaryotic or eukaryotic expression of an exogenous DNA. Purification and isolation is preferably achieved by chromatography on an anion exchanger, cation exchanger or a nickel chelate column.

The process according to the invention is particularly advantageous for the purification of plasminogen activators such as tissue plasminogen activators (t-PA) and derivatives (e.g. mutations and deletions) thereof. t-PA is described in EP-B 0 093 619 (13), derivatives of tPA are described in the U.S. Pat. No. 5,223,256 (53), WO 90/09437 (54) and T. J. R. Harris (1987) (20).

The ETI polypeptide can be produced according to methods familiar to a person skilled in the art. For this firstly a nucleic acid molecule (preferably DNA) is produced which codes for an ETI polypeptide which begins N-terminally with SEQ ID NO:4 or with a SEQ ID NO:4 extended N-terminally by methionine and codes for an ETI polypeptide. The ETI polypeptide has an amino acid sequence that is functionally analogous to SEQ ID NO:2, and contains a partial region that is more than 85% and preferably completely homologous to the region of amino acids 39–139 of SEQ ID NO:2 and two disulfide bridges. In this connection it is also possible to use a sequence which codes for the same polypeptide within the scope of the degeneracy of the genetic code and/or is complementary to this sequence. A nucleic acid is also preferably used which hybridizes under stringent conditions with SEQ ID NO:1 and which N-terminally codes for SEQ ID NO:4 or for a SEQ ID NO:4 extended N-terminally by methionine. The DNA is cloned in a vector that can be transferred into a host cell and replicated there. In addition to the ETI polypeptide sequence, such a vector contains operator elements which are necessary for the expression of the DNA. This vector which contains the inhibitor DNA and the operator elements is transferred into a vector which is able to express the DNA of the ETI polypeptide. The host cell is cultured under conditions which allow the expression of the ETI polypeptide. The ETI polypeptide is isolated from these cells. In doing so suitable measures ensure that the ETI polypeptide can adopt an active tertiary structure in which it exhibits inhibitor properties.

In this connection, as already set forth, it is not necessary that the ETI polypeptide has the exact amino acid sequence corresponding to SEQ ID NO:2 and SEQ ID NO:4. ETI polypeptides are equally suitable which have essentially the same sequence and are polypeptides with the activity of an inhibitor DE-3 from *Erythrina caffra*. However, it is essential that Val is replaced by Ser at the N-terminus. The amino acid sequences SEQ ID NO.2 and 4 are preferably used which, in the case of expression in prokaryotic host cells but not after eukaryotic expression, can contain an N-terminal methionine (SEQ ID NO:10). However, the methionine is also usually cleaved in *E. coli* since the sequence begins N-terminally with Met-Ser (Dalborge H. et al. (1990) (7)). Such a polypeptide in which the Met is cleaved off is preferred.

The invention also concerns an isolated nucleic acid which codes for an ETI polypeptide that reversibly and selectively binds serine proteases from a protein mixture and wherein the protein has an amino acid sequence which is functionally analogous to SEQ ID NO:2, has a partial region that is more than 85% homologous to the region of amino acids 39–139 of this sequence, has two disulfide bridges and begins N-terminally with SEQ ID NO:4 or with a SEQ ID NO:4 extended N-terminally by methionine. Such an isolated nucleic acid is preferably identical to SEQ ID NO:1 or to a nucleic acid that codes for the same polypeptide within the scope of the degeneracy of the genetic code. For expression in eukaryotic or prokaryotic host cells the nucleic acid contains eukaryotic or prokaryotic transcription or translation signals at the 5' end that are familiar to a person skilled in the art.

A nucleic acid is preferably used which hybridizes under stringent conditions with SEQ ID NO: 1 under standard conditions. Such standard conditions and methods for hybridization are known to a person skilled in the art and described for example by J. Sambrook et al. (1989) (38) and B. D. Hames, S. G. Higgins (1985) (19). The standard protocols described in these publications are usually used for this purpose. In particular reference is made to Sambrook, Section IX (40), both publications being a subject matter of the disclosure of this invention. Standardized stringent conditions are also described in Höltke and Kessler (1990) (24).

Preferred stringent conditions are given when the hybridization is carried out in the presence of 1 mol/l NaCl, 1% SDS and 10% dextran sulfate with subsequent two-fold washing of the filter at room temperature for 5 minutes in 2×SSC and a further washing step for 30 minutes. This further washing step can be carried out with 0.5×SSC, 0.1% SDS, preferably with 0.2×SSC, 0.1% SDS and particularly preferably with 0.1×SSC, 0.1% SDS at 65° C.

Modifications may be appropriate in order to facilitate the construction of vectors or to optimize the expression. Such modifications are for example:
  modification of the nucleic acid in order to introduce various recognition sequences for restriction enzymes in order to facilitate the steps of ligation, cloning and mutagenesis
  modification of the nucleic acid to incorporate preferred codons for the host cell extension of the nucleic acid by additional operator elements in order to optimize expression in the host cell.

The inhibitor is preferably expressed in microorganisms such as *E. coli*. However, expression in eukaryotic cells such as yeast, CHO cells or insect cells is also possible.

Biologically functional plasmids or viral DNA vectors are used for this purpose which contain the nucleic acid according to the invention. Prokaryotic or eukaryotic host cells are stably transformed or transfected with such vectors.

The expression vectors must contain a promoter which allows expression of the inhibitor protein in the host organism. Such promoters are known to a person skilled in the art and are for example the lac promoter (Chang et al. (1977) (26)), trp (Goeddel et al. (1980) (18)), λPL promoter (Shimatake et al., (1981) (41)) and T5 promoter (U.S. Pat. No. 4,689,406 (49)). Synthetic promoters are also suitable such as for example the tac promoter (U.S. Pat. No. 4,551,433 (48)). Coupled promoter systems are equally suitable such as for example the T7-RNA polymerase/promoter system (Studier et al., (1986) (44)). Hybrid promoters comprising a bacteriophage promoter and the operator region of the microorganism (EP-A 0 267 851 (11)) are also suitable. In addition to the promoter, an effective ribosome binding site is also required. In the case of *E. coli* this ribosome binding site is called the Shine-Dalgarno (SD) sequence (Shine et al. (1975) (42); J. Sambrook et al. (1989) (39)).

In order to improve expression it is possible to express the inhibitor protein as a fusion protein. In this case a DNA sequence which codes for the N-terminal part of an endogenous bacterial protein or for another stable protein is usually fused to the 5'end of the sequence coding for the inhibitor protein. Examples of this are lacZ, trpE.

After expression the fusion proteins are preferably cleaved with enzymes (e.g. factor Xa) (Nagai et al. (1984) (32)). Further examples of cleavage sites are the IgA protease cleavage site (WO 91/11520) (55)) and the ubiquitin cleavage site (Miller et al., (1989) (31)). In such cases the ETI polypeptide according to the invention can additionally contain one or several additional amino acids at the N-terminus. However, an ETI polypeptide is preferably used that contains no additional N-terminal amino acids and begins N-terminally with SEQ ID NO:4.

The recombinant protein which is at first obtained as inactive inclusion bodies can be converted into a soluble active protein by processes familiar to a person skilled in the art. For this purpose the inclusion bodies are for example solubilized with guanidinium hydrochloride or urea in the presence of a reducing agent, reduced, the reducing agent is removed for example by dialysis and the solubilized protein is renatured preferably using a redox system such as reduced and oxidized glutathione or mixed disulfides.

Such methods are described for example in U.S. Pat. No. 4,933,434 (52), EP-B 0 241 022 (16) and EP-A 0 219 874 (10).

It is also possible to secrete the proteins as active proteins from the microorganisms. A fusion protein is preferably used for this which is composed of the signal sequence that is suitable for secretion of proteins in the host organisms used (U.S. Pat. No. 4,336,336 (47)) and the nucleic acid which codes for the inhibitor protein. In this process the protein is either secreted into the medium (in the case of gram-positive bacteria) or into the periplasmatic space (in the case of gram-negative bacteria). It is appropriate to incorporate a cleavage site between the signal sequence and the sequence coding for the inhibitor which enables cleavage of the inhibitor protein either during the processing or in an additional step. Such signal sequences are for example ompA (Ghrayeb et al., (1984) (17)) and phoA (Oka et al. (1985) (33)).

The vectors additionally contain terminators. Terminators are DNA sequences which signal the end of a transcription process. They are usually characterized by two structural features: a reversely repetitive G/C-rich region that can intramolecularly form a double helix and a number of U (or T) residues. Examples are the trp attenuator and terminator in the DNA of the phages fd and rrnB (Brosius et al., (1981) (5)).

The expression vectors usually additionally contain a selectable marker in order to select transformed cells. Such selectable markers are for example the resistance genes for ampicillin, chloroamphenicol, erythromycin, kanamycin, neomycin and tetracyclin (Davies et al. (1978) (8)). Selectable markers that are equally suitable are the genes for substances that are essential for the biosynthesis of substances necessary for the cell such as histidine, tryptophan and leucine.

Numerous suitable bacterial vectors are known. For example vectors have been described for the following bacteria: *Bacillus subtilis* (Palva et al. (1982) (35)), *E. coli* (Aman et al. (1985) (1)); Studier et al. (1986) (44)), *Steptococcus cremoris* (Powell et al. (1988) (37)); *Streptococcus lividans* and *Streptomyces lividans* (U.S. Pat. No. 4,747,056 (50)).

In addition to prokaryotic microorganisms it is also possible to express the inhibitor protein in eukaryotes (such as for example CHO cells, yeast or insect cells). Yeast and insect cells are preferred as the eukaryotic expression system. Expression in yeast can be achieved by three types of yeast vectors (integrated $YI_p$ (yeast integrating plasmids) vectors, replicating $YR_p$ (yeast replicon plasmids) vectors and episomal $YE_p$ (yeast episomal plasmids) vectors. More details on this are described for example in S. M. Kingsman et al. (1987) (28).

Further genetic engineering methods for constructing and expressing suitable vectors are described in J. Sambrook et al. (1989) (39).

After production, the recombinant ETI is purified chromatographically on an anion exchanger such as a Q-Sepharose® column, a cation exchanger (e.g. based on sulfopropyl) or on a nickel chelate column as described for example in Porath, J. & Olin, B. (1983) (36).

Surprisingly a recombinant ETI polypeptide is obtained after this purification process which, when immobilized on BrCN-Sepharose, has an increased binding capacity and an increased specific inhibitory activity for t-PA and t-PA derivatives.

An ETI polypeptide produced and purified in this manner is obtainable by culturing prokaryotic or eukaryotic host cells which are transformed or transfected with an exogenous DNA sequence that codes for an ETI polypeptide that reversibly and selectively binds serine proteases from a protein mixture, the protein having an amino acid sequence which is functionally analogous to SEQ ID NO:2, a partial region thereof being more than 85% homologous to the region of amino acids 39–139 of this sequence, having two disulfide bridges and beginning N-terminally with SEQ ID NO:4 or with a SEQ ID NO:4 extended N-terminally by methionine, in a manner that allows the host cells to express the polypeptide under suitable nutrient conditions, and isolating the desired polypeptide which, compared to the natural ETI polypeptide from *Erythrina caffra*, has a higher binding capacity for human tissue plasminogen activator. The binding capacity is preferably between 1.25 and 1.6 MU/ml.

Such an inhibitor derivative preferably additionally has a specific inhibitory activity of 1.07 U/mg, preferably of 1.5

U/mg or more towards trypsin. This high activity is obtained after chromatographic purification on an anion exchanger, cation exchanger or on a nickel chelate column.

Moreover the invention concerns a process for the production of a recombinant ETI polypeptide by culturing prokaryotic or eukaryotic host cells which are transformed or transfected with an exogenous DNA sequence that codes for an ETI polypeptide that reversibly and selectively binds serine proteases from a protein mixture, the protein having an amino acid sequence which is functionally analogous to SEQ ID NO:2, a partial region thereof being more than 85% homologous to the region of amino acids 39–139 of this sequence, having two disulfide bridges and beginning N-terminally with SEQ ID NO:4, in a manner that allows the host cells to express the ETI polypeptide under suitable nutrient conditions, isolating the ETI polypeptide from the host cells and chromatographic purification on an anion exchanger, cation exchanger or on a nickel chelate column.

Serine proteases are purified using the recombinant ETI polypeptide according to methods familiar to a person skilled in the art (cf. e.g. F. J. Joubert (1987) (25)). For this purpose the ETI polypeptide is bound covalently to a matrix (e.g. CNBr-Sepharose column) and the protein mixture that contains the serine protease is applied to the column under neutral or weakly alkaline conditions and a chromatography is carried out. It is eluted by lowering the pH to ≦pH 5.5 or by using buffer solutions that contain chaotropic agents such as e.g. KSCN. The eluate has a protein purity of over 95% relative to the serine protease.

The immobilization of the inhibitor and all further process steps for purifying serine protease and t-PA can be carried out in an analogous manner to that of the inhibitor DE-3 isolated from *E. caffra*. Such processes are described for example in EP-B 0 218 479 (15), EP-B 0 112 122 (14), U.S. Pat. No. 4,902,623 (51). It is expedient to immobilize on an inert support, preferably on CNBr-Sepharose®.

The microorganisms DSM 3689 and DSM 5443 mentioned in the application have been deposited on 09.04.1986 (DSM 3689) and 13.07.1989 (DSM 5443) at the "Deutsche Sammlung von Mikroorganismen und Zellkulturen GmbH", Mascheroder Weg 1B, D-38124 Braunschweig.

The following examples, publications and sequence protocol further describe the invention the protective scope of which derives from the patent claims. The described methods are to be understood as examples which describe the subject matter of the invention even after modification.

EXAMPLE 1

Expression of ETI Polypeptide in *E. coli* a) Gene Synthesis

A corresponding nucleic acid sequence is derived from the amino acid sequence of the ETI polypeptide from *Erythrina caffra* (Joubert and Dowdle (1987) (27)) utilizing the codons preferred by *E. coli* and synthesized by the method of Beattie and Fowler (1991) (2). In order to facilitate cloning, a cleavage site for the restriction enzyme EcoRI is inserted at the 5'end and a cleavage site for the restriction enzyme HindIII is inserted at the 3'end. The synthesized nucleic acid was cleaved with the enzymes EcoRI and HindIII and ligated with the cloning vector pBS+ (Stratagene, US, Catalogue No. 211201 (43), derivative of the phage f1 and Stratagene's pBS plasmid with a $T_3$ and $T_7$ promoter gene, ampicillin resistance gene, f1 origin, ColE-1 origin, lacI gene, lacZ gene and a multiple cloning site) which was previously also digested with EcoRI and HindIII. The ligation mixture was transformed in *Escherichia coli*. The clones obtained were selected on ampicillin and analysed by restriction with the enzymes EcoRI and HindIII. The resulting clone, PBS+ETI, contains an additional EcoRI/HindIII fragment with a size of about 539 bp and has SEQ ID NO:9.

b) Expression Vector

The plasmid pBS+ETI was cleaved with the restriction enzymes EcoRI and HindIII and the fragment of 539 bp in size was isolated. The expression vector pBTac1 (Boehringer Mannheim GmbH, Catalogue No. 1081365 (3), based on pUC8, H. Haymerle et al. (1986) (21)) was also digested with the enzymes EcoRI and HindIII and the vector fragment of approximately 4.6 kb in size was isolated. Both fragments were ligated and transformed in *E. coli* (DSM 5443) together with the helper plasmid pUBS520 (Brinkmann et al. (1989) (4)) that contains the lac repressor gene. The clones were selected by means of the ampicillin or kanamycin resistance mediated by the plasmids. The plasmid pBTETI obtained contains an additional EcoRI/HindIII fragment with a size of 539 bp compared to the initial vector pBTac1 and can be used to express recombinant, non-modified ETI (recETI). DSM 3689 which already contains an $I^q$ plasmid can also be used in an analogous manner instead of DSM 5443. In this case the helper plasmid pUB520 is not required.

A fusion PCR was carried out for the N-terminal mutation and introduction of a new promoter. The promoter from the plasmid pDS46/RBII (commercially available from the Qiagen Company under the name pQE-6) was amplified using the oligonucleotides ETI-1 and ETI-2 (amplification product A). The synthetic sequence which codes for an ETI polypeptide was isolated from the plasmid pBTETI using the PCR primers ETI-3 and ETI-4, the primer ETI-3 being designed in such a way that the amplified product codes for an ETI polypeptide having the desired amino acid substitution (Ser) (amplification product B). Both amplification products were fused by means of PCR and with the aid of the primers ETI-1 and ETI-4. The fusion product was cleaved with the two restriction enzymes BamHI and HindIII and purified. The plasmid pA27fd, EP-A 0 382 174 (U.S. Pat. No. 5,223,256) (12) was (partially) treated with the two restriction enzymes BamHI and HindIII and the vector fragment of about 4600 bp in size was isolated. The vector fragment and fusion fragment were ligated and transformed together with the helper plasmid pUBS520 (Brinkmann et al. 1989 (4)) in *E. coli* C600+ (DSM 5443). The clones were selected by means of the ampicillin and kanamycin resistance mediated by the plasmids. The plasmid pETI-T2Lvs obtained contains an additional HindIII fragment of about 350 bp compared to the initial plasmid pBTETI.

TABLE 1

PCR primers

| Primer | Sequence 5'->3' | |
|---|---|---|
| ETI-1 | AAAGGATCCCTCGAGAAATCATAAAAA | (SEQ ID NO:5) |
| ETI-2 | CATAAGAATTCTGTTTCCTCTTTAATGAATTCTG | (SEQ ID NO:6) |
| ETI-3 | CAGAATTCTTATGTCATTATTAGA | (SEQ ID NO:7) |
| ETI-4 | AGAAGCTTTTATCAGCTG | (SEQ ID NO:8) | c) Expression of Recombinant ETI Polypeptide (SerETI) in *E. coli*

In order to examine the expression efficiency the *E. coli* strain DSM 5443 was cultured with the plasmids pETI-T2Lvs and pUBS520 in LB medium (Sambrook et al. (1989) (38)) in the presence of ampicillin and kanamycin (50 µg/ml final concentration in each case) to an optical density (OD) of 0.6 at 550 nm. The expression was initiated by addition of 5 mM IPTG. The culture was incubated for a further 4 hours. Subsequently *E. coli* were collected by centrifugation and resuspended in buffer (50 mM Tris-HCl pH 8, 50 mM EDTA); the *E. coli* were lysed by sonification. The insoluble protein fractions (inclusion bodies) were collected by centrifuging again and resuspended in the aforementioned buffer by sonification. The suspension was admixed with ¼ volume application buffer (250 mM Tris-HCl pH 6.8, 0.01 M EDTA, 5% SDS, 5% mercaptoethanol, 50% glycerol and 0.005% bromophenol blue) and analysed with the aid of a 12.5% SDS polyacrylamide gel. As a control the same preparation was carried out using a culture of *E. coli* (pETI-T2Lvs/pUBS520) which had not been admixed with IPTG and applied to the polyacrylamide gel. After staining the gel with 0.2% coomassie blue R250 (dissolved in 30% methanol and 10% acetic acid) and destaining the gel in a methanol-acetic acid mixture, a pronounced band with a molecular weight of about 22 kD is recognizable in the preparation of the IPTG-induced culture. This band cannot be found in the preparation of the *E. coli* cells which had not been induced.

EXAMPLE 2

Renaturation and purification of SerETI 50 g inclusion bodies (IBs) were solubilized with 0.1 M Tris/HCl, pH 8.5, 6 M guanidine, 0.1 M DTE, 1 mM EDTA (90 min at 25° C.) and dialysed against 3 mol/l guanidine/HCl after adjusting the pH value to 2.5 (HCl). The dialysate was centrifuged (SS34, 13000 rpm) and adjusted to a $c_{prot}$=36.9 mg/ml by concentration over a YM 10. A 1 l reaction vessel was filled with 0.1 M Tris/HCl, pH 8.5, 1 mM EDTA, 1 mM GSH, 0.1 mM GSSG. It was renatured at 20° C. at a time interval of 30 min by a 16-fold addition of the dialysate.

Purification of SerETI a) Over an Anion Exchanger

SerETI is renatured in 0.1 M Tris/HCl, pH 8.5, 1 mM EDTA, 1 mM GSH, 0.1 mM GSSG. The renaturate is diluted 1:2 with $H_2O$, adjusted to pH 8.0 with HCl and applied to a Q-Sepharose® column equilibrated with 50 mM Tris/HCl, pH 8.0 (5 mg protein/ml gel). After washing the column with equilibration buffer and with 50 mM $Na_2HPO_4/H_3PO_4$, pH 8.0 (five column volumes each time) it is eluted with 50 mM $Na_2HPO_4/H_3PO_4$, pH 8.0, 0.2 M NaCl.

b) Over a Cation Exchanger

Renatured SerETI was adjusted to pH 4.0 by addition of HCl and dialysed against 50 mM NaOAc/HCl, pH 4.0 (Cross Flow). The dialysate was centrifuged (13000 rpm, 30 min, SS 34) and applied to a TSK-SP column (cation exchanger with sulfopropyl side chains, Merck, Darmstadt, Germany, volume 15 ml) which had been equilibrated with 50 mM NaOAc/HCl, pH 4.0. After washing the column with equilibration buffer and with 50 mM NaOAc/HCl, pH 4.0, 0.1 M NaCl it is eluted with 50 mM NaOAc/HCl, pH 4.0, 0.2 M NaCl.

The purity of the eluate was examined by means of SDS-PAGE and RP-HPLC.

Result

Ser-ETI binds to the TSK-SP column under the conditions used and can be eluted with 0.2 M NaCl. SDS-PAGE and RP-HPLC analysis yield a purity of >95%.

EXAMPLE 3

Comparison of the Specific Activity of SerETI, recETI and of ETI From the Seeds of *Erythrina caffra*

SerETI, recETI and ETI isolated from the seeds of *E. caffra* [ETI (seeds)] were dialysed against 50 mM $Na_2HPO_4/$ $H_3PO_4$, pH 8.0, 0.25 M NaCl and adjusted to a protein concentration of 1.0 mg/ml. The protein concentration was determined by measuring the UV absorbance at 280 nm ($\epsilon$=1.46 $cm^2$/mg).

Determination of the ETI Activity

The inhibition of trypsin by ETI is measured using N-α-benzoyl-L-arginine-4-nitroanilide (BAPA) as the substrate. 40 μl of a trypsin solution (0.13 mg/ml 2 mM HCl) is mixed with 60 μl test buffer (0.1 M Tris/HCl, pH 8.0) and 100 μl ETI solution in a quartz cuvette and incubated for 5 min at 30° C. After addition of 800 μl BAPA solution (10 mg BAPA×HCl/10 ml test buffer) the increase in absorbance per minute is determined at 405 nm.

The ETI activity is determined according to the following formula:

$$U/\text{ml}=[1-A_{sample}/A_{trypsin}] \cdot C_{trypsin} \cdot 0.328 \cdot P$$

$A_{sample}$: increase in absorbance/min of inhibited sample
$A_{trypsin}$: increase in absorbance/min of uninhibited trypsin
$C_{trypsin}$: trypsin concentration in the test mixture
P: predilution of the ETI solution

| Protein | specific activity (U/mg) |
|---|---|
| ETI (seeds) | 0.88 |
| SerETI | 1.5 |
| rec.ETI | 1.07 |

Result: the specific activity of SerETI is 50% higher than the specific activity of ETI isolated from the seeds of *E. caffra* by classical processes.

EXAMPLE 4

Coupling ETI to CNBr Sepharose®

170 mg purified SerETI or ETI (seeds) or recombinant ETI (produced analogously to example 1 and 2) were dialysed against 0.05 M $H_3BO_3$/NaOH, pH 8.0, 0.5 M NaCl (coupling buffer) and mixed with 7.5 g CNBr-Sepharose® (swollen overnight in 500 ml 1 mM HCl, subsequently suction filtered and suspended in coupling buffer). The suspension was incubated for 90 min at room temperature, suction filtered and shaken overnight with 400 ml 0.1 M Tris/HCl, pH 8.0. The SerETI-Sepharose® was drained and equilibrated with 0.7 M arginine/$H_3PO_4$, pH 7.5.

EXAMPLE 5

Purifying a Recombinant Plasminogen Activator rPA rPA: recombinant tPA derivative comprising the kringle 2 and protease domains (produced according to EP-A 0 382 174, (U.S. Pat. No. 5,223,256) (12))

54 mg recombinant plasminogen activator rPA (protein concentration determined by means of the absorbance at 280 nm, extinction coefficient 1.69 $cm^2$/mg) was applied to ETI-Sepharose equilibrated with 0.7 M arginine/$H_3PO_4$, pH 7.5. After washing with equilibration buffer and with 0.3 M arginine/$H_3PO_4$, pH 7.0 (five column volumes in each case) it was eluted with 0.3 M arginine/$H_3PO_4$, pH 4.5. The content of plasminogen activator in the eluate was in each case determined with S 2288 as the substrate, cf. example 6.

EXAMPLE 6

Comparison of the Binding Capacity of SerETI-Sepharose and ETI (Seeds)-Sepharose for r-PA ETI (seeds) and Ser-ETI were coupled to CNBr-Sepharose ff according to the instructions of the Sepharose manufacturer (Pharmacia, Freiburg). The final columns were equilibrated with 0.7 mol/l Arg/H$_3$PO$_4$, pH 7.5, loaded with 2 MU r-PA/ml gel and, after washing with 5 CV 0.7 mol/l Arg/H$_3$PO$_4$, pH 7.5, 0.5 M NaCl and 5 CV 0.3 mol/l Arg/H$_3$PO$_4$, pH 7.0, they were eluted with 0.3 mol/l Arg/H$_3$PO$_4$, pH 4.5. The binding capacity was determined as the eluted rPA (MU/ml gel). Each gel was loaded five times and eluted. The gels were regenerated under standard conditions between the individual steps.

| Run | Binding capacity MU/ml seeds-ETI-Seph. | Ser-ETI-Seph. |
| --- | --- | --- |
| 1 | 1.04 | 1.28 |
| 2 | 0.95 | 1.35 |
| 3 | 1.08 | 1.53 |
| 4 | 1.01 | 1.48 |
| 5 | 0.98 | 1.49 |

The data summarized in the table show that Ser-ETI-Sepharose produced by coupling Ser-ETI to CNBr-Sepharose has a 1.5-fold higher binding capacity for r-PA than the seed-ETI-Sepharose formed by coupling seed-ETI to CNBr-Sepharose.

Determination of the activity: (Kohnert et al. (1992) (29)). 200 μl buffer (0.1 mol/l Tris HCl pH 7.5, 0.15% Tween® 80) and 200 μl rPA solution diluted with buffer to a concentration of 1–12 μg/ml are incubated for 5 minutes at 37° C. The test is started by addition of 200 μl S2288 (6 mmol/l (H-D-Ile-Pro-Arg-P-nitroanilide dehydrochloride, Kabi Vitrum, Sweden)) which had also been incubated at 37° C. The amidolytic activity is calculated from the increase in absorbance at 405 nm within the first 2.5 minutes with an extinction coefficient for p-nitroaniline of 9750 l/mol/cm.

List of References

1) Aman et al.; Gene 40 (1985) 183
2) Beattie und Fowler; Nature 352 (1991) 548–549
3) Boehringer Mannheim GmbH, Katalog Nr. 1081365
4) Brinkmann et al.; Gene 85 (1989) 109–114
5) Brosius et al.; J. Mol. Biol. 148 (1981) 107–127
6) Chang et al.; Nature 198 (1977) 1056
7) Dalborge, H. et al.; FEBS Letters 266 (1990) 1–3
8) Davies et al.; Ann. Rev. Microbiol. 32 (1978) 469
9) DE-A 44 24 171
10) EP-A 0 219 874
11) EP-A 0 267 851
12) EP-A 0 382 174 (U.S. Pat. No. 5,223,256)
13) EP-B 0 093 619
14) EP-B 0 112 122
15) EP-B 0 218 479
16) EP-B 0 241 022
17) Ghrayeb et al.; EMBO J. 3 (1984) 2437
18) Goeddel et al.; Nuc. Acids Res. 8 (1980) 4057
19) Hames, B. D.; Higgins, S. G.; Nucleic Acid Hybridization—A practical approach (1985) IRL Press, Oxford, England
20) Harris, T. J. R.; Protein Engineering 1 (1987) 449–458
21) Haymerle, H. et al.; Nucl. Acid Res. 14 (1986) 8615–8624
22) Heussen, C.; J. Biol. Chem. 259 (1984) 11635–11638
23) Heussen, C.; Haemostasis 11 (1982) P47 (Supplement)
24) Höltke und Kessler; "The DIG system user's guide for filter hybridization" (1990), Boehringer Mannheim GmbH, Germany.
25) Joubert, F. J.; Thrombosis and Haemostasis 57 (3) (1987) 356–360
26) Joubert, F. J.; Int. J. Biochem. 14 (1982) 187–193
27) Joubert, F. J.; Phytochemistry 21 (1982) 1213–1217
28) Kingsman, S. M. et al.; Tibtech 5 (1987) 53–57
29) Kohnert, U. et al.; Protein Engineering 5 (1992) 93–100
30) Lehle, K. et al.; J. Mol. Biol. 239 (1994) 276–284
31) Miller et al.; Bio/Technology 7 (1989) 698
32) Nagai et al.; Nature 309 (1984) 810
33) Oka et al.; Proc. Natl. Acad. Sci. USA 82 (1985) 7212
34) Onesti, S. et al.; J. Mol. Recogn. 5 (1992) 105–114
35) Palva et al.; Proc. Natl. Acad. Sci. USA 79 (1982) 5582
36) Porath, J. & Olin, B.; Biochemistry 22 (1983), 1621–1630
37) Powell et al.; Appl. Environ. Microbiol. 54 (1988) 655
38) Sambrook et al.; Molecular Cloning: A laboratory manual (1989) Cold Spring Harbor Laboratory Press, New York, USA
39) Sambrook et al., "Expression of cloned genes in E. coli" in Molecular Cloning: A laboratory manual (1989) Cold Spring Harbor Laboratory Press, New York, USA
40) Sambrook, J. et al; Section IX, "A hybridization of radiolabelled probes to immobilized nucleic acid", in Molecular Cloning: A laboratory manual (1989), Cold Spring Harbor Laboratory Press, New York, USA, 947–962
41) Shimatake et al.; Nature 292 (1981) 128
42) Shine et al.; Nature (1975) 25434;
43) Stratagene, US, Catalogue No. 211201
44) Studier et al.; J. Mol. Biol. 189 (1986) 113
45) Teixeira et al.; Biochimica et Biophysica Acta 1217 (1994) 16–22
46) Teixeira et al.; Biochemica et Biophysica Acta 1217 (1994) 23–28
47) U.S. Pat. No. 4,336,336
48) U.S. Pat. No. 4,551,433
49) U.S. Pat. No. 4,689,406
50) U.S. Pat. No. 4,747,056
51) U.S. Pat. No. 4,902,623
52) U.S. Pat. No. 4,933,434
53) U.S. Pat. No. 5,223,256
54) WO 90/09437
55) WO 91/11520

We claim:

1. A polypeptide which has the inhibitory activity of an inhibitor DE-3 from *Erythrina caffra*, wherein said polypeptide reversibly and selectively binds serine proteases, and wherein said polypeptide is obtained by a process comprising the steps of culturing prokaryotic or eukaryotic host cells which are transformed or transfected with a nucleic acid which encodes the polypeptide under conditions which allow the host cells to express the polypeptide, and isolating the polypeptide, wherein the polypeptide has an amino acid sequence which has the same inhibitory activity as a polypeptide with an amino acid sequence according to SEQ ID NO: 2, is encoded by a DNA sequence which has a region which hybridizes under stringent hybridization conditions with a DNA sequence encoding amino acids 39–139 of SEQ ID NO: 2, has two disulfide bridges and begins N-terminally with SEQ ID NO: 4 or with SEQ ID NO: 4 which is extended N-terminally by methionine, wherein said stringent hybridization conditions are 1 mol/l NaCl. 1% SDS and 10% dextran sulfate with subsequent washing in 2×SSC at room temperature and further washing in 0.5×SSC and 0.1% SDS at 650° C.

2. The polypeptide according to claim 1, wherein said polypeptide begins N-terminally with SEQ ID NO:4.

3. A polypeptide according to claim 1, wherein the polypeptide is encoded by a nucleic acid selected from the group consisting of
   a) a nucleic acid according to SEQ ID NO:1, and
   b) a nucleic acid which hybridizes under stringent hybridization conditions with a DNA sequence complementary to the DNA sequence shown in SEQ ID NO:1, wherein said nucleic acid begins N-terminally with a nucleic acid sequence encoding SEQ ID NO:4, wherein said stringent hybridization conditions are 1 mol/l NaCl, 1% SDS and 10% dextran sulfate with subsequent washing in 2×SSC at room temperature and further washing in 0.5×SSC and 0.1% SDS at 65° C.

4. A polypeptide according to claim 1, wherein said polypeptide has a binding capacity for tissue plasminogen activators of 1.25 MU/ml or more.

5. A polypeptide which has the sequence shown in SEQ ID NO:2.

6. A matrix for purifying serine proteases, comprising a polypeptide immobilized on a solid phase, wherein said polypeptide has the inhibitory activity of an inhibitor DE-3 from *Erythrina caffra*, wherein said polypeptide reversibly and selectively binds serine proteases, and wherein said polypeptide is obtained by a process comprising the steps of culturing prokaryotic or eukaryotic host cells which are transformed or transfected with a nucleic acid which encodes the polypeptide under conditions which allow the host cells to express the polypeptide, and isolating the polypeptide, wherein the polypeptide has an amino acid sequence which has the same inhibitory activity as a polypeptide with an amino acid sequence according to SEQ ID NO: 2, is encoded by a DNA sequence which has a region which hybridizes under stringent hybridization conditions with a DNA sequence encoding amino acids 39–139 of SEQ ID NO:2, has two disulfide bridges and begins N-terminally with SEQ ID NO: 4 or with SEQ ID NO: 4 which is extended N-terminally by methionine, wherein said stringent hybridization conditions are 1 mol/l NaCl. 1% SDS and 10% dextran sulfate with subsequent washing in 2×SSC at room temperature and further washing in 0.5×SSC and 0.1% SDS at 650° C.

* * * * *